United States Patent [19]

Dryden

[11] Patent Number: 5,144,972
[45] Date of Patent: Sep. 8, 1992

[54] STOPCOCK WITH A PROTECTIVE ASSEMBLY

[76] Inventor: Gale E. Dryden, 5835 N. Tacoma, Indianapolis, Ind. 46220

[21] Appl. No.: 769,970

[22] Filed: Oct. 2, 1991

[51] Int. Cl.$^5$ ............................................. F16L 55/18
[52] U.S. Cl. ...................... 137/15; 137/315; 137/381; 137/625.47; 251/904
[58] Field of Search ........... 251/904; 137/381, 625.47, 137/15, 315

[56] References Cited

U.S. PATENT DOCUMENTS

| | | | |
|---|---|---|---|
| 3,834,372 | 9/1974 | Turney | 251/904 |
| 3,872,882 | 3/1975 | Fjermestad et al. | 137/381 |
| 4,307,748 | 12/1981 | Mathias | 137/381 |
| 4,314,586 | 2/1982 | Folkman | 251/904 |
| 4,445,530 | 5/1984 | Meixell | 137/381 |
| 4,590,967 | 5/1986 | Schmitt et al. | 137/381 |

*Primary Examiner*—A. Michael Chambers
*Attorney, Agent, or Firm*—Woodard, Emhardt, Naughton, Moriarty & McNett

[57] ABSTRACT

A stopcock with a locking connector protective assembly for selectively controlling the passage of sterile medicinal fluids from a plurality of sources and comprising a body having a plurality of input arms with male or female locking connector tips, an output arm with a male locking connector tip, a rotor located inside the body and having a handle and rotatable about an axis in the body and having a rotor lumen and having channels or holes that may be aligned with the arm lumens as indicated by pointers. A self-sealing injection port is provided which covers the rotor lumen. A locking connector protective assembly is mounted on the input arms to prevent touch contamination and may be retrofitted to current stopcocks, and retained by the locking connector tip. A telescoping resilient coil variably expands to enclose the locking connector tip when the tip is not in use and retracts sufficiently to allow access to the locking connector tip for connections to a complementary locking connector tip. A rim at the proximal end of the coil has resilient locking tabs permitting installation over a locking connector tip flange, but resisting removal therefrom, and a lid that may be flipped off the rim for access to the locking connector tip and which is retained by a flexible lid retainer link connected to the rim.

24 Claims, 4 Drawing Sheets

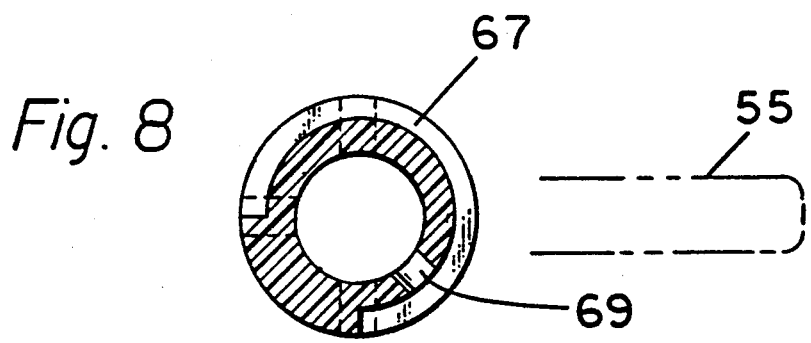
Fig. 8
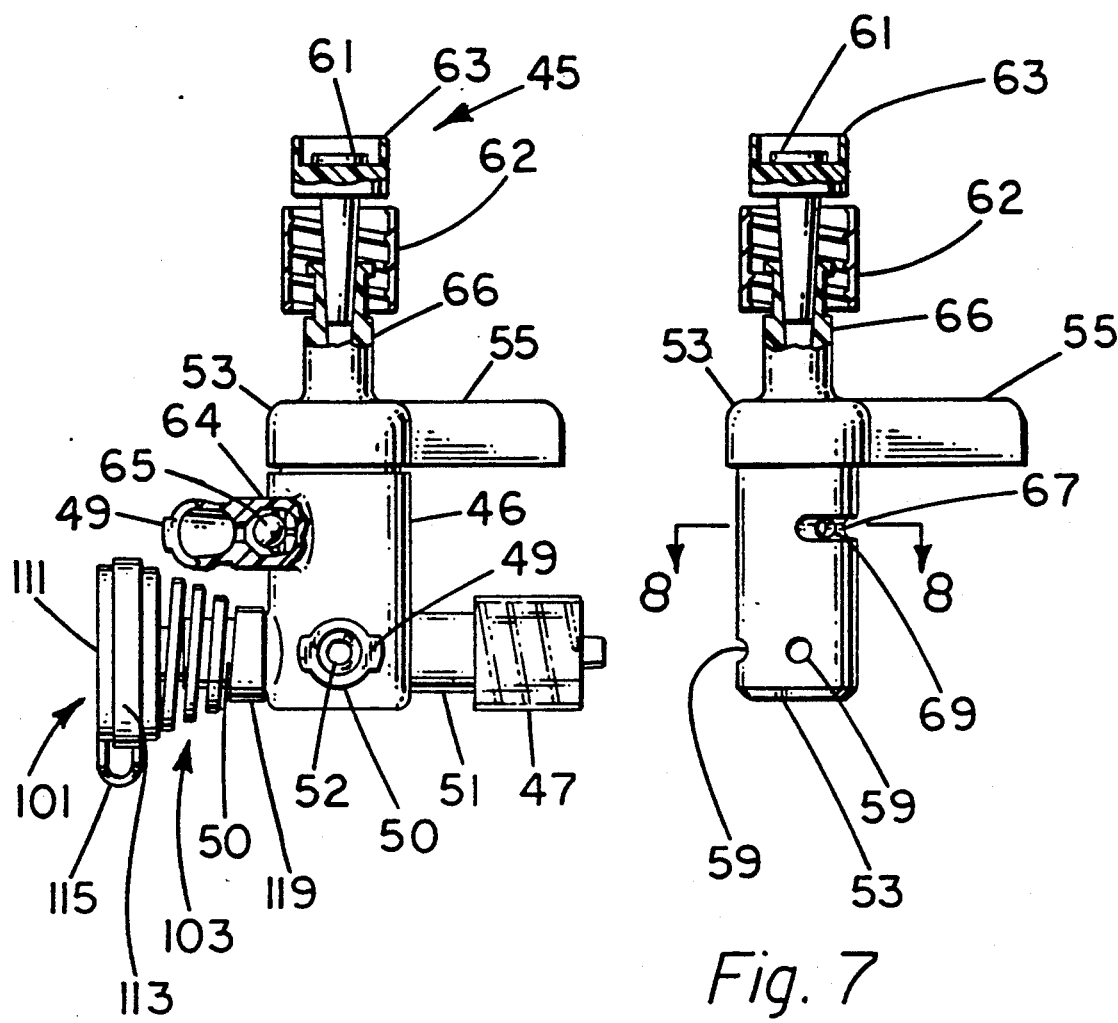
Fig. 6
Fig. 7

STOPCOCK WITH A PROTECTIVE ASSEMBLY

BACKGROUND OF THE INVENTION

The present invention relates generally to a stopcock and more specifically to an improved stopcock and a protective assembly for connection of fittings on the stopcock and which may be retrofitted to current stopcocks.

Stopcocks are widely used to direct the flow of multiple compatible intravenous (IV) solutions into one IV line. A stopcock allows the user increased flexibility to select from among several input lines and various combinations of the above to run into the output line or to stop the IV flow altogether. It is advantageous to run multiple lines into one line because this can dilute out a particular drug that is irritating to patients and it can also decrease the need for multiple IV sites in a patient.

While IV stopcocks are widely used because of their advantages, they have several disadvantages. It is difficult to handle current stopcocks without touch contamination because of their small size with short connector arms that are unprotected from touch contamination. Another disadvantage of current stopcocks is because of the short handle lengths on the rotors that are turned to select the flow desired through the stopcocks. A further disadvantage is the small internal fluid passageways that restrict the flow of viscous fluids, especially blood. This can substantially increase the time it takes to infuse these fluids. Because of this, it may be necessary to utilize pumps to force the fluids through these restricted passageways. It is frequently necessary to push IV drugs through injection ports while the stopcock is in place. Therefore, the lack of an injection port on commercially available stopcocks may cause inconvenience or require additional IV lines to be placed in the patient. The placement of additional lines may cause the patient discomfort and may be difficult for healthcare workers, as well, because of the patient's physiological condition. Most stopcocks are of limited input capacity and have only two input arms and one output arm. This is frequently insufficient, so multiple stopcocks are required in combination to supply sufficient input line capacity. A single stopcock of greater input arm capacity is contemplated according to my invention so that multiple stopcocks are not required. One feature of the invention is a stopcock with connector arms having standard locking connector tips with a locking connector protective assembly over the female locking connector tips. Another feature is increased length of the arms and handle and increased capacity for input lines. A further feature may include input arms that contain a backflow check valve and that lie on a different plane than the other arms.

SUMMARY OF THE INVENTION

One embodiment of the present invention relates to an improved stopcock with a locking connector protective assembly. The stopcock has a body with a plurality of input arms that have male or female locking connector tips and an output arm with a male locking connector tip. A rotor is placed inside the body and has a handle which is used to rotate the rotor in the body. The rotor has a rotor lumen and channels for passage of fluids. A self-sealing injection port covers the rotor lumen. The arms and channels are located in the same plane as defined by the rotation of the channels in the rotor to permit the passage of fluids between the two.

A locking connector protective assembly is placed over the female locking connector tip and encloses the female locking connector tips. The assembly has a coil with a proximal and distal end. The proximal end of the coil has a closure with a lid and rim where the lid has means for covering the rim and is connected to the rim by a flexible lid retainer link. The rim also has means to secure the assembly to the locking connector tip. The distal end of the coil abuts the body of the stopcock.

A preferred embodiment of the invention has enlarged and lengthened arms and handle for improved operation and contains pointers to indicate to the user which lines are open and which lines are closed. The stopcock also has enlarged lumens to increase the flow of viscous fluids, decrease the need for pumps and also has a locking connector protective assembly which may also be retrofitted to stopcocks. In another embodiment of this invention, one or more self-sealing injection ports are included with the stopcock and cover the rotor lumen or may be attached via locking connectors to the arms of the stopcock. Further embodiments of this invention include a stopcock having an input arm with an integral back check valve to prevent back flow into the input line, and a stopcock with a bottom output arm.

One object of this invention is to prevent touch contamination of the locking connector tips. Another object of this invention is to simplify the operation of the stopcock by using longer arms and handles, providing self-sealing injection ports, providing larger stopcock lumens and channels and location stops. A further object of this invention is to allow retrofit of current stopcocks, other IV line connectors or adapters with the locking connector protective assembly. Related objects of the present invention are disclosed in the following description of the preferred embodiments.

BRIEF DESCRIPTION OF THE DRAWINGS

FIG. 6 is a side view of a four arm stopcock with back flow check valve.

FIG. 7 is a side view of the rotor of the stopcock in FIG. 6.

FIG. 8 is a section of the rotor which illustrates the orientation of the groove to the handle.

DESCRIPTION OF THE PREFERRED EMBODIMENT

Figure 1:
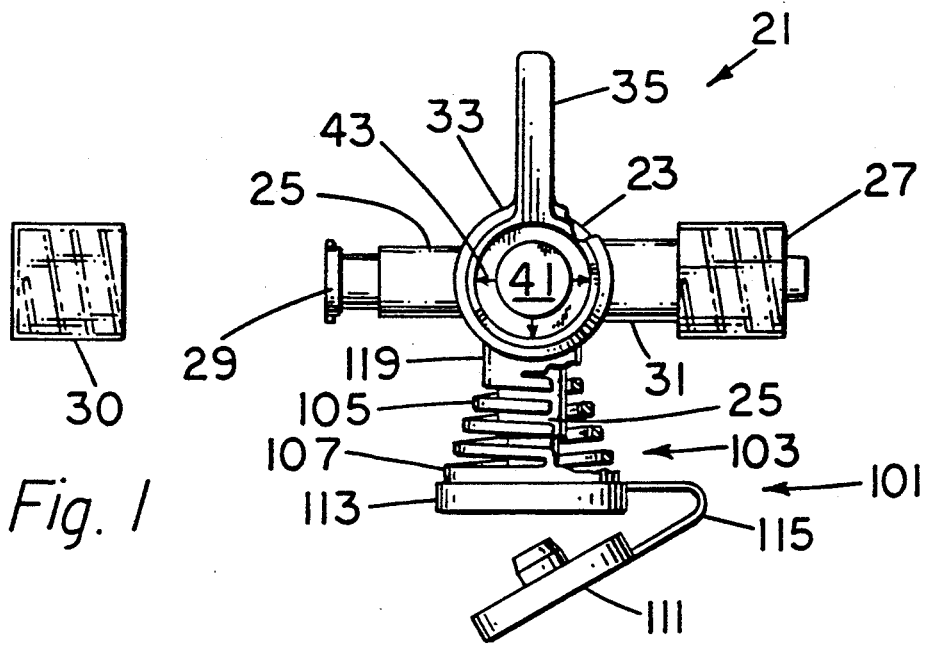
FIG. 1 is a top view of a three limb stopcock with a locking connector protective assembly.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device and method, and such further applications of the principles of the invention as illustrated therein being contemplated as would normally occur to one skilled in the art to which the invention relates.

Figure 2:
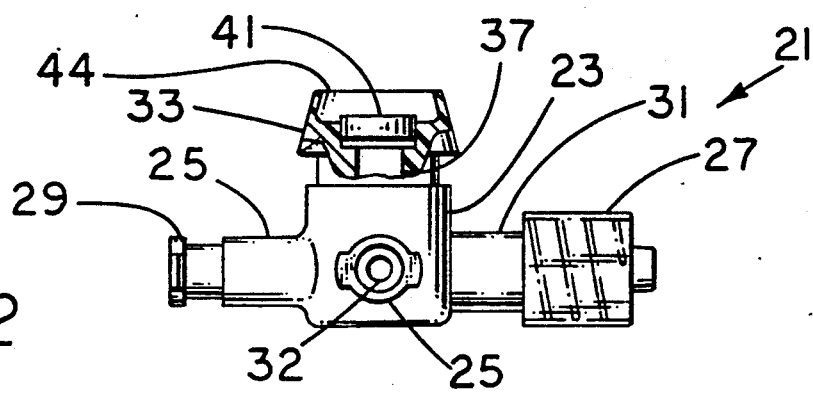
FIG. 2 is a side view of a three limb stopcock with the locking connector protective assembly omitted.
Figure 3:
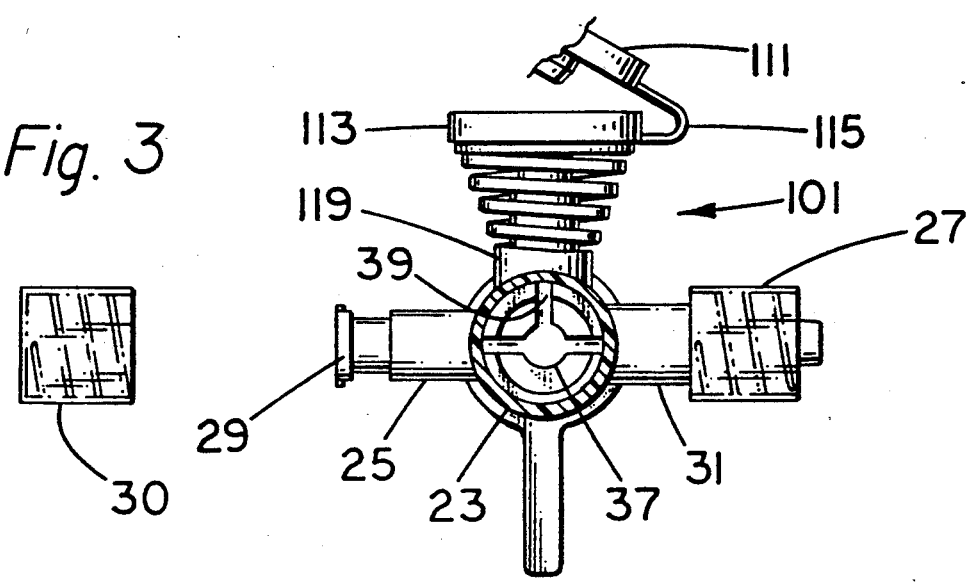
FIG. 3 is a bottom view of a three limb stopcock with a locking connector protective assembly and with the bottom of the stopcock body broken away to show the bottom of the rotor.
Figures 4, 5:
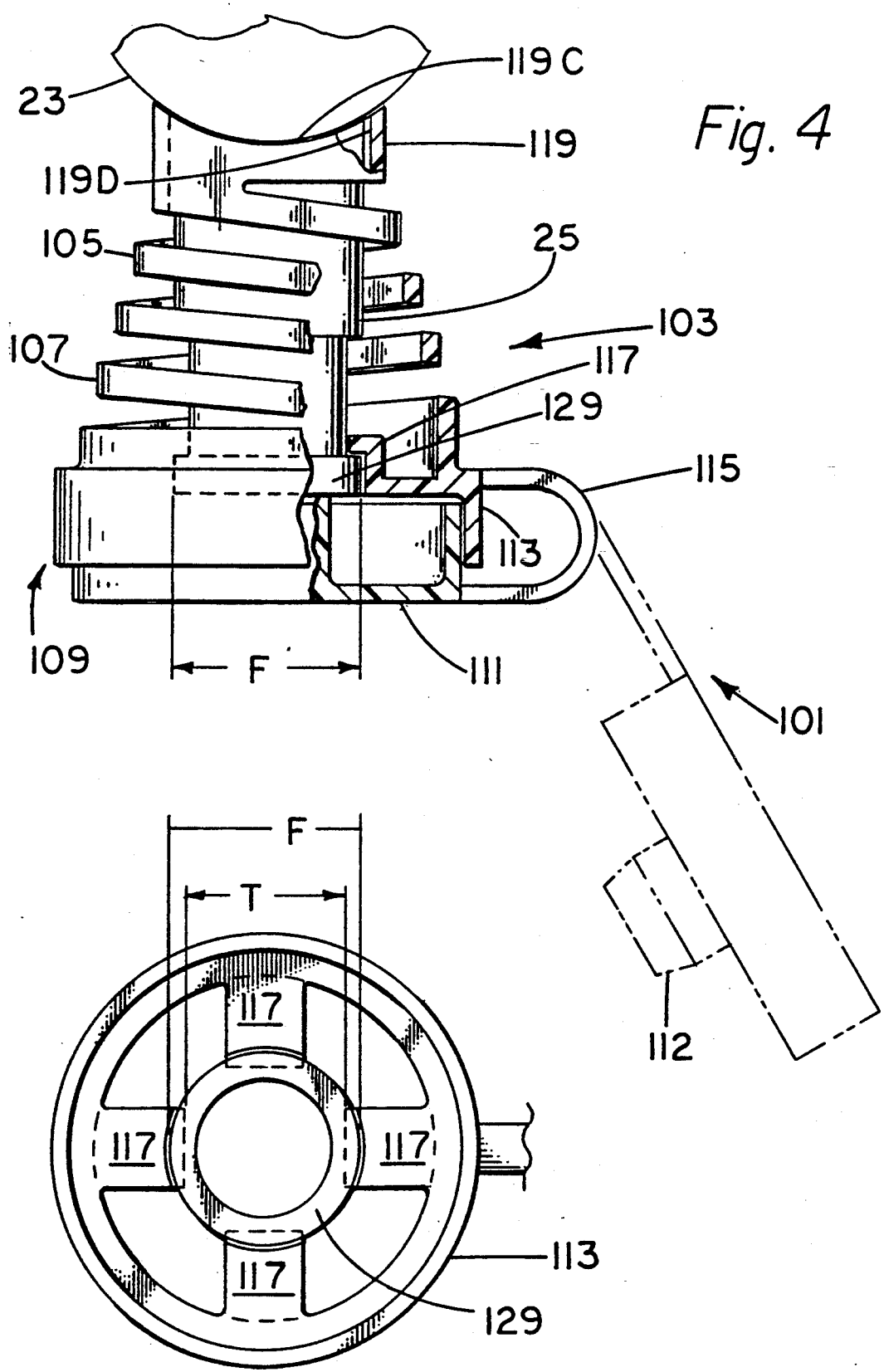
FIG. 4 is an enlarged top view of the locking connector protective assembly.
FIG. 5 is an axial view on the same scale as FIG. 4 showing the female locking connector tip of the FIGS. 1-3 embodiment with the protective assembly on it but the lid omitted for simplification of drawing.

FIGS. 1-3 illustrate a first embodiment of the present invention. The embodiment is shown in top, side and bottom view. The three arm stopcock 21 is illustrated with the locking connector Protective assembly 101. The stopcock has a body 23 with input arms 25 that have female locking connector tips 29, and an output arm 31 with a male locking connector tip 27. The arms have arm lumens 32 for passage of sterile fluids. A rotor 33 extending down inside the body 23 has a handle 35 which is used to rotate the rotor in the body. The rotor has a rotor lumen 37 from top to bottom and radial passageways 39 communicating with the lumen at the rotor bottom for passage of fluids. The passageways may be radial holes or channels as illustrated in FIG. 3. A self-sealing injection port plug 41 covers the top portion of the rotor lumen and provides needle access to the rotor lumen. The injection port plug is made from a pliable, needle-pierceable, self-sealing material and is similar to rubber stoppers that are used to cover vials of injectable drugs. The ends of the arms are located in the same plane as defined by the outer ends of the holes or channels in the rotor to permit the passage of fluids between the two. Pointers 43 are placed on the top of the rotor to indicate the selection of input or output lines connected to the stopcock. A car plug 30 is normally connected to the unused female locking connector tip and is constructed like a male locking connector tip 27, except that it has no lumen. A locking connector protective assembly 101 is placed over the female locking connector tip as shown in FIGS. 1 and 3 (and is omitted in FIG. 2 in order to show an end view of a female locking connector tip without the protector) and is shown in FIG. 4 in greater detail.

The rotor 33 is rotatable inside the body 23 by grasping the handle 35 and an input arm 25, an output arm 31 or the body 23 and turning the handle either clockwise or counter clockwise until the pointers 43 indicate the desired combination of input arms 25 and output arm 31 are open or closed to the flow of fluids. The handle may be turned so that all, none, or a portion of the input arm lumens are in communication with the lumen of the output arm. It is contemplated that the locking connectors shall be compatible with Luer Lok ™ connectors. Standard male locking connector tips on input lines may be connected to female locking connector tips such as 29 on the stopcock to provide a secure, fluid tight connection. The arms on the invention are at least 2.5 cm long to provide greater ease in connection of IV lines to the connectors on the stopcock.

Referring to the FIG. 2, a side view of the stopcock 21 is shown with the locking connector protective assembly removed to reduce the complexity of the drawing. A port rim 44 and an input arm 25 with an arm lumen 32 are also illustrated.

Although FIG. 3, shows the passageways as channels on the bottom of the rotor, and extending up the outside of the rotor to the plane of the inner ends of the arms, the passageways from the rotor lumen to the arms can be radial holes from the wall of the rotor 33 to the rotor lumen 37 in other embodiments.

The handle 35 is at least 2 cm in length to provide greater ease in manipulation of the rotor 33 in the body 23. The operator can grasp the handle 35 and turn the rotor about an axis in the body 23 to select the desired alignment of channels with the input and output arms as indicated by pointers 43 on the rotor to direct the flow of the fluids as desired. In FIG. 2, a part of the body at the top is broken away to show a self-sealing injection port plug 41 that covers the rotor lumen 37. The outer ends of the passageways 39 are in the same rotational plane as the corresponding arms in the body, and may be aligned with the arm lumens 32 to allow fluid flow between the rotor lumen 37 through the passageway 39 to the arm lumen 32. The arm lumens 32 and passageways 39 are approximately the same cross-sectional area for decreased restriction and increased fluid flow.

In this embodiment, the locking connector protective assembly 101 is positioned over the female locking connector tip 29 on the input arms 25, but not the male locking connector tips 27 since the male tips are largely enclosed by their conventional design and are much less susceptible to touch contamination than female locking connector tips. Although the stopcock illustrated in FIGS. 1-3 includes three arms, this embodiment may contain from three to five arms where the input arms are in the same plane as defined by the rotation of the passageways in the rotor. Other embodiments of this invention may include input or output arms on differing planes of rotation defined by the rotation of the rotor and two or more input arms 25 with male locking connector tips 27 or female locking connector tips 29, and may have self-sealing injection port plugs 41 connected to the invention by locking connectors.

Referring to FIGS. 4 and 5, a top view of the locking connector protective assembly 101 and an axial view thereof are illustrated. A coil 103 consisting of a plurality of turns has a proximal (to the user) end 107 with a closure 109 thereon. The proximal end of the coil is referred to as such since this end is manipulated by the operator. The closure is comprised of a rim 113 with resilient locking tabs 117, a lid 111 that fits into the rim 113 and a flexible lid retainer link 115 that is attached to the rim and the lid. The lid 111 has a stopper 112 that fits into the end of the female locking connector tip. The lid 111 may be pushed into the female locking connector tip to plug the lumen, or flipped away from the tip and retained by the flexible lid retainer link 115. The resilient locking tabs 117 project inward from the rim 113 so that the distance T (FIG. 5) between the tips of the tabs is less than the diameter F of the outer flange of a standard female locking connector tip 129. The rim 113 and the resilient locking tabs 117 fit over the the female locking connector tip 129 and retain the locking connector protective assembly 101 on the female locking connector tip. The distal end 105 of the coil 103 has a base 119 which abuts the body of the stopcock. The inside diameter of the inner face 119D of base ring 119 is greater than diameter F so the protective assembly can be easily pushed over the tip 129 and into position with the concave face 119C in contact with the body 23. The coil 103 is tapered so that it is a larger diameter on the proximal portion 107 and decreases in diameter towards the distal portion 105. This taper allows the coil to flatten into one plane as it is compressed.

A coil is one embodiment that may be utilized to allow the closure 113 to be pushed toward the body and return to a position that allows the closure to cover the female locking connector tip. Resilient means other than a coil may be used for this purpose. A spongy means, a resilient sheet or a resilient axially slit cylinder may also be substituted for the illustrated coil in different embodiments.

The locking connector protective assembly 101 functions to inhibit touch contamination of the female locking connector tip 129 by the operators' hands during connection of locking connectors. The locking connector protective assembly 101 may be retrofitted to prior art stopcocks or other fluid handling tubing or adaptors, by fitting the assembly over the female locking connector tip 129 where it is retained by the resilient locking tabs 117 projecting from the rim 113. The coil 103 extends over the input arm and female locking connector tip 129, and the closure 109 covers the access route to the female locking connector tip 129. When access to the female locking connector tip 129 is desired, the rim 113 is pushed in toward body 23, and lid 111 is pulled from the lumen of tip 29 and retained by the flexible lid retainer link 115. The coil 103 is compressed to allow access to the locking connector. A male locking connector tip may then be screwed onto the female locking connector tip after the removal of the cap plug 30 (if present as described in FIG. 1). The bias in the coil 103 due to its compression, is released, whereby the coil portion 103 extends the closure to a position partially encircling the male/female locking connector junction to provide a protective cover. If it is desired to disconnect the male/female connection, this may be accomplished by compression of the coil to allow access to the connectors and disconnection thereof by using a twisting motion to separate the locking connector tips followed by the insertion of a plug into the unused female locking connector tip (if desired). After the plug is inserted, the coil spring compression is released and the lid is placed onto the rim so that the locking connector protective assembly is returned to its original configuration.

Referring to FIGS. 6, 7 and 8, a side view of a stopcock 45 with the locking connector protective assembly 101 described in FIG. 4, and a rotor 53, is illustrated. The stopcock has a body 46 with two input arms 50 that lie in the same plane and have female locking connector tips 49, and an output arm 51 with a male locking connector tip 47. The arms have arm lumens 52 for the passage of the fluid. The stopcock 45 also has an input arm 64 (which is shown in a partial cutaway) with a back flow check valve 65. This arm is located on a plane different from the other arms and communicates with the rotor lumen by groove 67 in the rotor and running ¾ of the circumference of the rotor in the same plane as the input ar 64 with which it is aligned and by a radial passage 69 extending radially outward from the rotor lumen to the groove. Other portions of the stopcock and locking connector protective assembly are as described above with reference to the previous drawing figures. The rotor has a handle 55 which is used to rotate the rotor in the body. A port rim 63 surrounds the self-sealing injection port plug 61 which forms the top surface and covers the lumen of a male locking connector 62 that locks onto a female locking connector 66 on top of the rotor and which provides access to the rotor lumen.

When a primary fluid source is connected to the input arm 64, the back flow check valve 65 is useful to avoid back flow into the input line from the other IV lines. This valve avoids back flow into the primary source by secondary input lines that may be run on pumps which exert greater pressure than the primary line. This embodiment of the invention with four arms is useful to reduce the number of conventional stopcocks normally needed in combination to provide sufficient input lines into one output line. In this embodiment, the input line with the back check valve 65 is open to the rotor lumen for ¾ of its travel because the groove 67 runs ¾ of the circumference of the rotor and the line is closed for ¼ of the rotation of the rotor in the body. Groove 67 along the exterior circumference of the rotor 53 and communicating with the input arm 64 in its rotational plane during ¾ rotational travel of the rotor is one of the methods that a particular input arm or output arm may either be selected for fluid flow or blocked off from fluid flow. The orientation of the groove 67 to the handle 55 is illustrated in FIG. 8.

Figure 9:
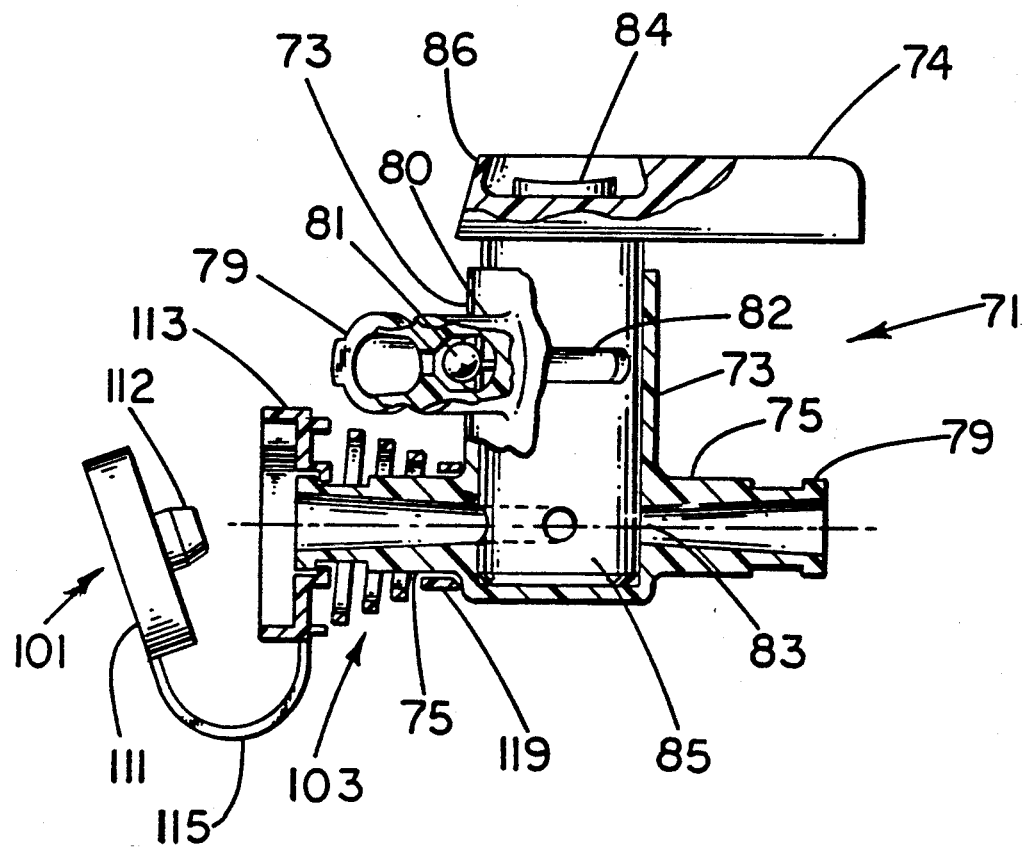
FIG. 9 is a side view cut away diagram of a four arm stopcock with a back flow check valve and self-sealing concave injection port plug.

A further embodiment of the present invention is illustrated in FIG. 9 which utilizes a countersunk injection port having a self-sealing injection port plug with a concave rubber face. This embodiment is similar to the stopcock of FIG. 6 except that the concave self-sealing injection port plug 84 covers the rotor lumen, rather than attaching to a locking connector, and has a concave shape. Also included is a body 73 and an input arm 80 (which is shown in a partial cutaway) with a back check valve 81 open to the rotor lumen for ¾ of its travel because groove 82 in the rotor 85 runs ¾ of the circumference of the rotor and communicates with the rotor lumen as described in FIGS. 7 and 8. In this embodiment of the invention, two input arms 75 and the output arm (not shown) are positioned in the same plane 83 of rotation of the corresponding radial holes in the rotor. The input arm 80 with a backflow check valve 81 and rotor groove 82 are in a plane of rotation different from that of the other input arms.

Although several embodiments of the invention are described, one skilled in art could practice alternate embodiments of the invention by varying the number of input arms on differing planes of rotation of the rotor in the body, as well as their orientation, and length of the grooves, or vary the locking connector protective assembly to provide a functional stopcock. Therefore, while the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A locking connector protective assembly comprising:
   a coil having a proximal end and a distal end, said proximal end having a closure;
   said closure including a rim and a lid to cover the rim, and the closure having means for securing said assembly to a female locking connector tip of a fluid handling system;
   said closure further including a flexible lid retainer link connected to said rim an said lid, wherein said lid includes means to plug into a lumen of the locking connector tip;
   said means for securing said assembly to said locking connector tip comprising four resilient locking tabs having tips that project inward from said rim such that the distance between said tips is less than the diameter of the outer flange of a standard Luer Lok female locking connector tip; and wherein said proximal coil end has a larger diameter than said coil end and said coil tapers from said proximal coil end toward said distal coil end such that said coil is resiliently compressible into a flat shape.

2. A locking connector protective assembly for enclosing a locking connector tip having a flange and a lumen comprising:

a resilient portion having a proximal and a distal end, said proximal end having a closure;

said closure being configures to cover the flange and lumen of the locking connector tip to thereby prevent touch contamination of said connector tip;

the closure including a rim, a lid, and a flexible lid retainer link connected to said lid and said rim;

said lid including means for plugging said lumen at said connector tip; and said rim including means for securing said assembly to said locking connector tip.

3. A locking connector protective assembly comprising;

a coil having a proximal end and distal end, said proximal end of said coil having a closure, said closure including a lid, a rim and having means for securing said assembly to a female locking connector tip of a fluid system wherein such locking connector tip has a lumen for passage of fluids therethrough, and an outer flange.

4. The locking connector protective assembly to claim 3 wherein said closure further includes a flexible lid retainer link connected to said rim and said lid, and said lid has means to plug into the locking connector tip lumen.

5. The locking connector protective assembly of claim 4 wherein said means for securing said assembly to said locking connector tip comprises four resilient locking tabs having tips that project inward from said rim such that the distance between said tips is less than the diameter of said outer flange.

6. A method for reducing touch contamination of locking connections comprising the steps of;

providing a female locking connector having an arm and a lumen and an outer flange, a male locking connector, and the assembly of claim 1;

positioning said assembly over said female locking connector to inhibit touch contamination of said locking connector during connection thereof;

sliding said assembly over said female locking connector along said arm until said resilient locking tabs lock onto said outer flange of said female locking connector thereby providing a touch contamination barrier around said locking connector;

obtaining access to said female locking connector by removing said lid and compressing said coil with minimal risk of touching a portion of said female locking connector tip; and connecting said male and female locking connectors and releasing said coil compression after locking said connectors to allow said protective assembly to extend to the male and female locking connector junction and; and after use separating said locking connectors by compression of said coil, disconnecting said locking connectors from each other, releasing said coil compression and pushing said means to plug into said lumen at said locking connector tip to return the locking connector protective assembly to its original configuration.

7. A method for reducing touch contamination of sterile locking connections comprising the steps of:

providing a female locking connector having an arm, and an arm lumen and an outer flange on the arm, a male locking connector having an arm lumen, and the assembly of claim 2;

positioning said assembly over said female locking connector;

sliding said assembly over said female locking connector along said arm until said means for securing said assembly engages said outer flange of said female locking connector arm thereby providing a touch contamination barrier around said locking connector;

obtaining access to said female locking connector by removing said lid and collapsing said resilient portion with minimal risk of touching a portion of said female locking connector tip; and connecting said male and female locking connectors and releasing said resilient portion after locking said connectors to allow said assembly to extend to the male and female locking connector junction and; after use separating said locking connectors by collapsing said resilient portion, disconnecting said locking connectors from each other, releasing said resilient portion compression and pushing said means for plugging into said lumen and returning the locking connector protective assembly to its original configuration.

8. A stopcock for selectively controlling the passage of sterile fluids from a plurality of sources comprising:

a body having a plurality of input arms with male or female locking connector tips, an output arm with a male locking connector tip an each of said input arms and said output arm having an arm lumen;

a rotor positioned inside the body and having a handle, and rotatable about an axis in the body and having a rotor lumen and having a plurality of passageways therein, and a self-sealing injection port covering said rotor lumen, said arm lumens and said passageways having portions located in the same plane for communication therebetween upon rotation of said rotor; and a locking connector protective assembly surrounding at least one of the arms and its locking connector tip and having a resilient portion having a proximal and a distal end, said proximal end of said resilient portion having a closure including a rim and a lid, said closure covering said locking connector tip thereby preventing touch contamination of said connector tip; and said lid including a stopper plugged into said arm lumen at said locking connector tip, and said closure having a flexible lid retainer link connecting said lid to said rim, and said rim having means to secure said assembly to said locking connector tip.

9. The stopcock of claim 8 wherein the resilient portion is a plastic coil.

10. The stopcock of claim 8 wherein the coil is tapered to resiliently collapse into a plane.

11. The stopcock of claim 8 wherein said self-sealing injection port has a male locking connector tip and said rotor has a female locking connector tip and said self-sealing injection port is attached to said rotor by connection of said male locking connector tip on said self-sealing injection port to said female locking connector tip on said rotor.

12. The stopcock of claim 11 wherein one or more of said plurality of input arms with locking connector tips are constructed for connection by locking connectors to said self-sealing injection ports with male locking connectors.

13. The stopcock of claim 8 wherein said passageways have approximately the same cross-sectional area as said arm lumens.

14. The stopcock of claim 8 wherein said number of arms ranges from 3 to 5.

15. The stopcock of claim 8 wherein said rotor has pointers to indicate the selection of input arms communicating with the output arm.

16. The stopcock of claim 15 wherein said rotor may be turned to a position whereby all of said arm lumens are in communication with said rotor lumen via said passageways.

17. The stopcock of claim 16 wherein said rotor may be turned to a position whereby said arm lumen of said output arm is not in communication with said rotor lumen.

18. The stopcock of claim 8 wherein said arms are at least 2.5 cm. in length and said handle is at least 2 cm. in length.

19. The stopcock of claim 8 wherein all of said input arms and said output arm lie on the same plane.

20. A stopcock for selectively controlling the passage of sterile fluids from a plurality of sources comprising:
 a body having a plurality of input arms with male or female locking connector tips, an output arm with a male locking connector tip and each of said input arms and said output arm having an arm lumen wherein said arm lumens provide passageways for fluids through said connector tips and all of said input arms and said output arm lie on the same plane;
 a rotor positioned inside the body and having a handle, and rotatable about an axis in the body and having a rotor lumen and having a plurality of passageways therein, and a self-sealing injection port covering said rotor lumen, said arm lumens and said rotor passageways having portions located in the same plane for communication therebetween upon rotation of said rotor;
 a locking connector protective assembly that encloses at least one of said locking connector tips and having a resilient portion with a proximal and a distal end, said proximal end having a closure including a rim and a lid and a flexible lid retainer link connecting said lid to said rim, said lid having means for covering said connector tip end, and said rim having means to secure the assembly to the locking connector tip;
 an input arm having a backflow check valve and an arm lumen and said input arm having a backflow check valve which lies on a different plane than the other arms;
 a groove on said rotor for a portion of its circumference that lies in the same plane as said input arm with a backflow check valve; and
 a radial passage in said groove wherein said groove communicates with said input arm with backflow check valve when said groove is positioned under said arm lumen of said input arm with a backflow check valve and said groove communicates with said rotor lumen through said radial passage.

21. The stopcock of claim 20 wherein said groove runs three-fourths of the circumference of said rotor.

22. The stopcock of claim 20 wherein the number of arms ranges from 3 to 6.

23. A stopcock for selectively controlling the passage of sterile fluids from a plurality of sources comprising;
 a body having a plurality of arms with male or female locking connector tips, each of said arms having an arm lumen and at least one of said arms having an outer flange on its locking connector tip, with a portion of the flange facing the stopcock body;
 a rotor positioned inside the body and having a handle, and rotatable about an axis in the body and having passageways therein, said arm lumens and said passageways having portions located in the same plane for communication therebetween upon rotation of said rotor; and
 a locking connector protective assembly surrounding said at least one of the arms and its locking connector tip and having a resilient portion having a proximal and a distal end, the distal end normally abuttingly engaging the stopcock body, said proximal end of said resilient portion having a rim around the outer flange of the arm to inhibit touch contamination of said connector tip; and
 the resilient portion having a locking portion at the rim abuttingly engaging the portion of the outer flange facing the stopcock body whereby the resilient portion between the proximal and distal end normally holds the rim in position around the outer flange, but enables intentional displacement of the rim axially of the arm.

24. The locking connector protective assembly of claim 23 wherein:
 the said outer flange is that of a standard Luer Lok female locking connector tip; and
 the distance between the stopcock body and the body-facing portion of the flange, compared to the distance between the distal end and the locking portion of the resilient portion is such as to require resilient deformation of the resilient portion between the proximal end and the distal end to displace the rim axially of the arm an amount sufficient to enable connection of a mating connector to the connector tip of the arm.

* * * * *